United States Patent [19]

Fox

[11] Patent Number: 4,695,274
[45] Date of Patent: Sep. 22, 1987

[54] PROTECTED HYPODERMIC NEEDLE

[76] Inventor: Richard L. Fox, 1804 Rockefeller La., Redondo Beach, Calif. 90278

[21] Appl. No.: 824,879

[22] Filed: Jan. 31, 1986

[51] Int. Cl.4 ............................................. A61M 5/32
[52] U.S. Cl. .................................... 604/198; 604/263
[58] Field of Search ............... 604/198, 199, 192, 263

[56] References Cited

U.S. PATENT DOCUMENTS

| | | | |
|---|---|---|---|
| 3,134,380 | 5/1964 | Armao | 604/198 |
| 3,354,881 | 11/1967 | Bloch | 604/199 X |
| 4,425,120 | 1/1984 | Sampson et al. | 604/198 |
| 4,507,118 | 3/1985 | Dent | 604/198 |

Primary Examiner—John D. Yasko
Attorney, Agent, or Firm—Beehler, Pavitt, Siegemund, Jagger, Martella & Dawes

[57] ABSTRACT

A safety needle attachment for a syringe body assembly makes use of a needle holder with a needle fixed in the holder and the holder so constructed that it can, if necessary, be applied to and removed from the syringe body assembly at will. The needle is initially entirely surrounded by a protecting jacket which is releasably interlocked with the holder. When the needle is to be used, the interlock is released and the jacket in effect telescoped over the holder to project the needle through a membrane over the end of the jacket to a working position. After use the jacket is returned to its protecting position and there interlocked in place. Thereafter for those occasions where the attachment is removable from the body assembly, it can be removed for disposal.

4 Claims, 7 Drawing Figures

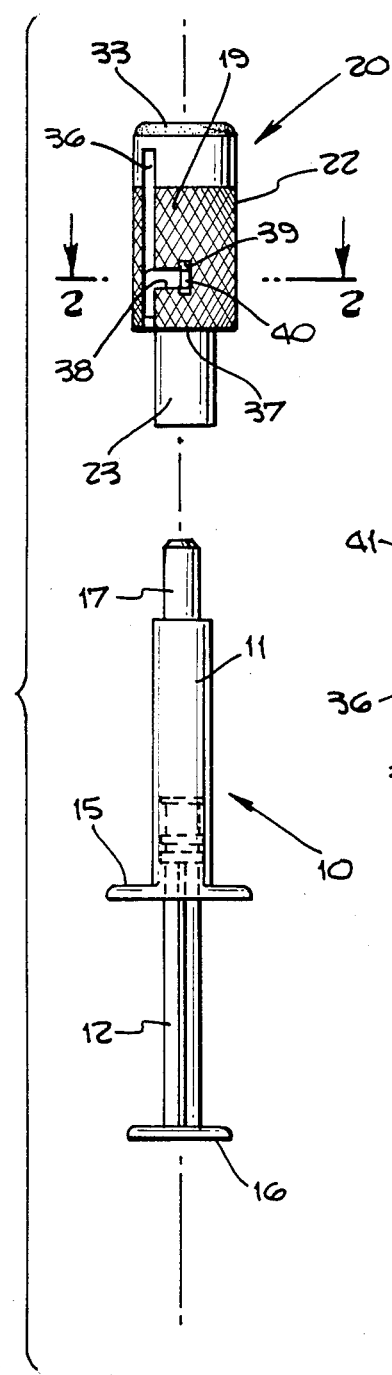
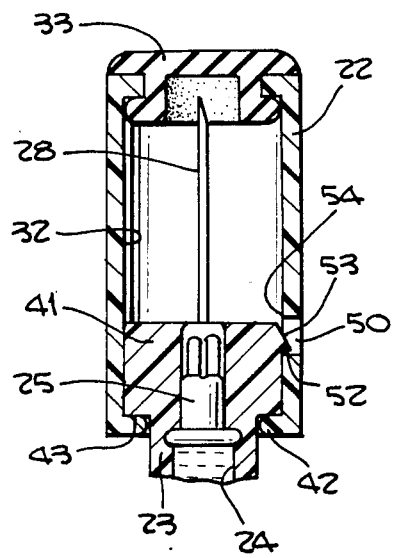
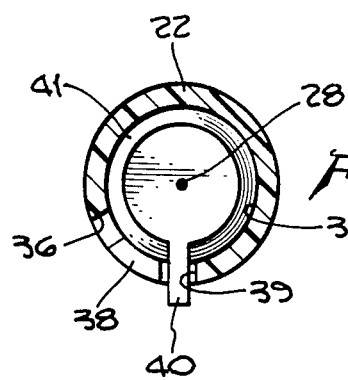
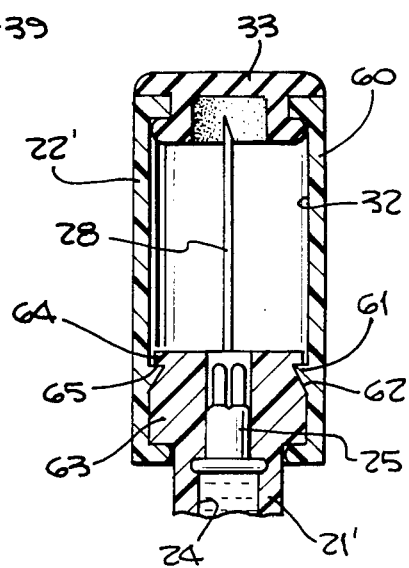

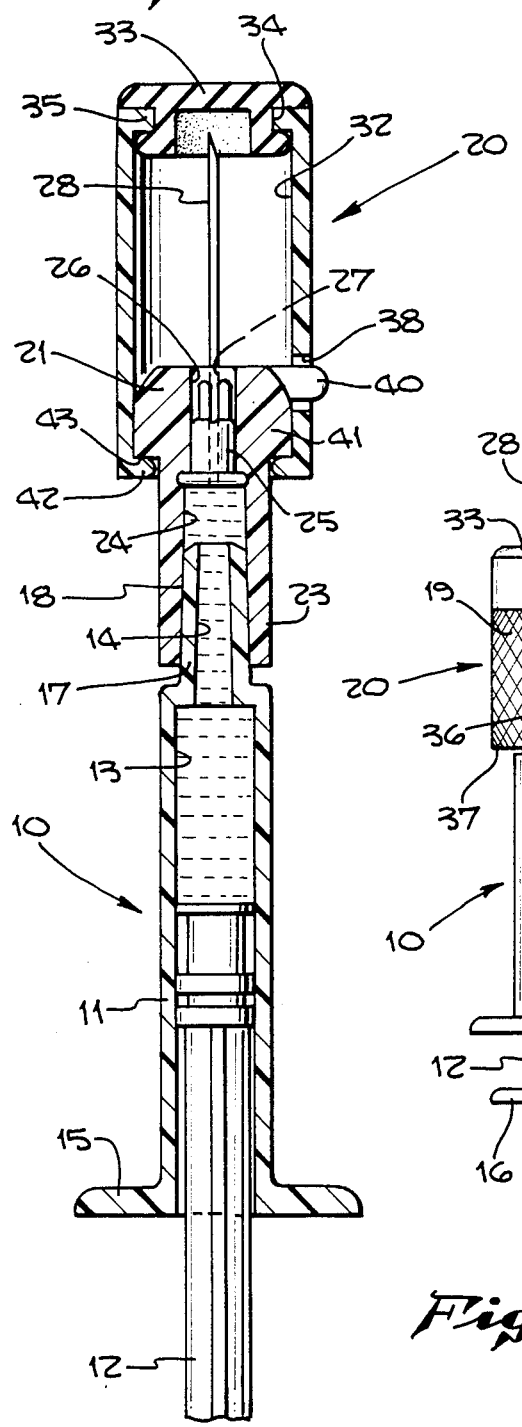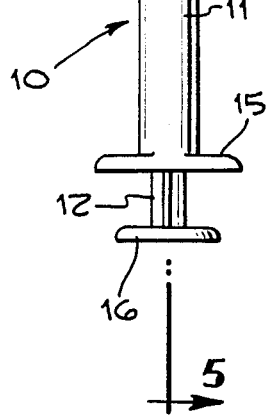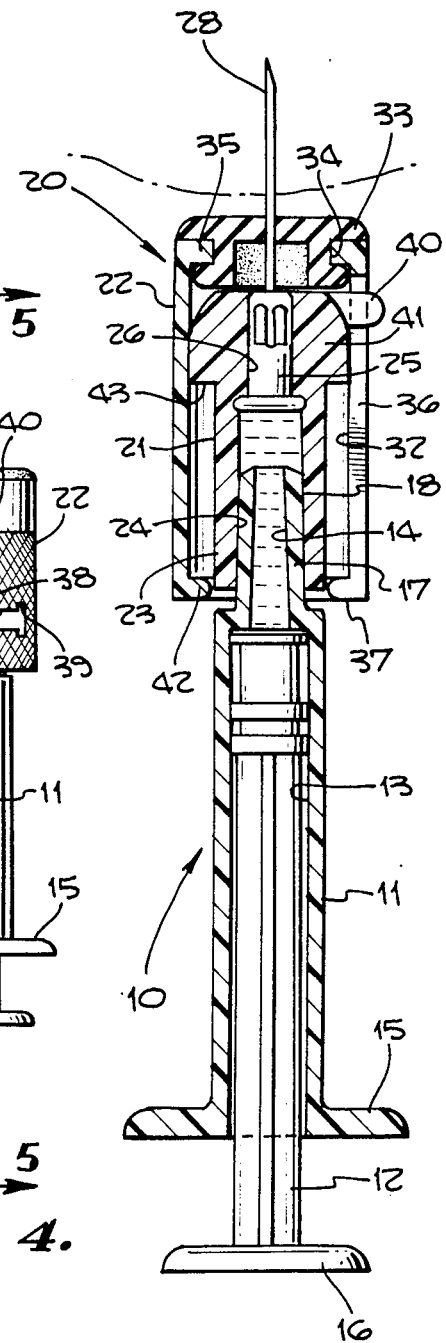

PROTECTED HYPODERMIC NEEDLE

The invention has reference primarily to hypodermic-type syringes. A syringe is aptly defined as an instrument suited for the injection of medicine or the withdrawal of body fluids and consists of a hollow barrel fitted with a plunger and a hollow needle.

It should be noted that the invention is applicable both to hypodermic syringes which have a permanently attached needle and also syringes to which syringes a needle may be removed and reattached as needed. Although the invention is directed primarily to disposable types of hypodermic syringes because of their widespread use and convenience, it is applicable also to non-disposable types of syringes for ease of use and safety.

Irrespective of the precise use to which a needle may be put, when exposed, either prior to or following a work operation, the needle presents an accidental puncture hazzard to the operator. An exposed needle is also a contamination hazzard not only to the operator but others, including the person injected. It is the intent of this invention to drastically reduce the hazzards referred to as well as other hazzards which may be attributed to an exposed needle.

Heretofore, disposable hypodermic syringes have been manufactured with a protective detachable cover over the needle which can be too easily removed as, for example, should the syringe be dropped or knocked against some object.

In the interest of maintaining a high degree of sanitation and safety, there has been a common practice of re-attaching the protective cover over the needle if the syringe is not to be used immediately. Reattachment can result in damaging or dulling the needle point. Also where the needle has already been used, for sanitary practice, it should be disposed of. Needle covers tend to be small in diameter and therefore require a concentrated effort to align the needle with the opening of the protective cover before sliding the cover over the needle. Often, preoccupation of the user with other matters at hand, or lack of concentration on aligning the cover over the needle may create a serious hazzard. Accidental needle puncture is not uncommon in the medical field and has become of much greater concern recently due to possible contraction of previously communicable diseases.

It is therefore among the objects of the invention to provide a new and improved protective or safety type hypodermic syrings which is equipped with a protective or safety type guard around the needle whenever it is not in use, but in an arrangement which permits the guard to be moved out of the way during use and then reapplied on completion of the use.

Another object of the invention is to provide a new and improved protective type hypodermic syringe wherein inadvertent contact with the needle is protected against prior to and subsequent to use and in particular on those occasions when the needle assembly or the entire syringe body itself, may be disposed of after use.

Another object of the invention is to provide a new and improved protective hypodermic syringe of the disposable type which is of simple, inexpensive construction conductive to disposal after use.

Further included among the objects of the invention is to provide a new and improved protective hypodermic type syringe wherein the protecting features are compact so as not to impair effective use of the needle, while at the same time being sufficiently simple to operate, inexpensive to encourage disposal after a single use and provide maximum safety against accidental puncture, needle damage, or needle contamination.

Further among the objects of the invention is to provide a new and improved needle attachment for a protective hypodermic syringe assembly readily applicable to conventional syringes and of a type readily adjustable to permit the needle to be used when called upon and so arranged that the protective feature can be immediately reapplied subsequent to use.

Further included among the objects of the invention is to provide a new and improved needle attachment for a hypodermic type syringe which is capable of carrying the needle during application to the syringe body assembly prior to and during use and thereafter is readily removable from the body of the syringe so that the needle resides in a safety package during removal from the syringe barrel and thereafter while being disposed of.

With these and other objects in veiw, the invention consists of the construction, arrangement and combination of various parts of the device, serving as sundry examples of several embodiments of the invention whereby the objects comtemplated are attained as hereinafter disclosed in the specification and drawings and pointed out in the appended claims.

In the drawings:

FIG. 1 is an elevational exploded view showing the device with relation to a syringe.

FIG. 2 is a cross-sectional view on the line 2-2 of FIG. 1.

FIG. 3 is a vertical sectional view showing the device in place on a syringe and in retracted adjustment.

FIG. 4 is a side elevational view of the device in place on a syringe and in operative adjustment.

FIG. 5 is a vertical sectional view similar to FIG. 3 but with parts in operational adjustment.

FIG. 6 is a fragmentary vertical sectional view of a second form of the device in retracted adjustment.

FIG. 7 is a fragmentary sectional view of a third form of the device in retracted adjustment.

In one embodiment of the invention chosen for the purpose of illustration there is shown a conventional syringe body assembly indicated generally by the reference character 10, consisting in the main of a barrel 11 and a plunger 12 cooperable with the barrel. The barrel provides a chamber 13 for fluid from which there is a passage 14 at one end of the exterior. At the other end of the chamber the barrel is provided with a handhold flange 15, to be used in cooperation with an operating disc 16 at the corresponding end of the plunger. The passage 14 is contained within a nosepiece 17 on the exterior of which is a gentle tapered surface 18.

In one embodiment of the invention as shown in FIGS. 1 to 5 there is provided a removable needle attachment 20, consisting in the main of a needle-holding member 21 and a safety jacket 22. The needle-holding member 21 in effect carries the safety jacket 22 so that a mounting projection 23, in which there is a tapered recess 24, serves as a means for releasably mounting the needle attachment on the nosepiece 17 of the barrel by application of the tapered recess 24 over the nosepiece 17, as shown in FIG. 1.

The needle-holding member is provided with a plug 25 fitting snugly within a bore 26, the plug being provided with a pass-through hole 27 at the outer end of which a hypodermic needle 28 is mounted.

The safety jacket 22 previously identified has a pocket 32 long enough to accommodate the full exposed length of the needle 28. At the outside end of the pocket 32 is an end cap 33 of an appropriate rubber or synthetic plastic material, of permeable character, capable of being pierced by the needle 28 and resealing the pierced aperture when the needle is withdrawn. There is an annular retention recess 34 surrounding the end cap 33 for reception of an annular projection 35 extending inwardly from the side wall of the safety jacket 22.

To enable the needle 28 to be projected outwardly through the end cap 33 to a working position during use, the safety jacket 22 must be capable of being moved inwardly toward the mounting projection 23 of the needle-holding member 21, while at the same time maintaining a degree of engagement. To accomplish this in the embodiment of FIGS. 1 to 5, there is provided a longitudinally extending guide slot 36 in the wall of the safety jacket 22, the guide slot extending throughout most of the length of the wall and exiting at an inside edge 37. In communication with the guide slot 36 is a transverse extension 38 which may, if desired, terminate in an interlock notch 39. The transverse extension 38 and its interlock notch is adapted to receive a guide tab 40 which protrudes radially outwardly from a head 41 of the needle-holding member 21. The guide tab 40 is of a size enabling it to slide endwise within the guide slot 36 and to move transversely within the transverse extension 38.

Of additional consequence is the provision of an annular inwardly extending flange 42 at the inside end of the safety jacket 22 which is adapted to abut against the annular shoulder 43 at the inside end of the head 41.

For operation of the needle attachment disclosed in the form of invention of FIGS. 1 to 5, needle attachments of the type described normally are adjusted in the position shown so that the needle 28 is entirely contained within the safety jacket 22. Continuance of this relationship is assured by having the guide tab 40 projected into the transverse extension 38 of the guide slot 36 to a position where it may lodge in the interlock notch 39. In this arrangement there is no likelihood that the needle will be inadvertently extended through the permeable end cap 33 to an exposed position.

When the syringe is to be used, the needle attachment 20 is applied to the syringe body assembly 10 by pressing the tapered recess 24 of the mounting projection 23 over the nosepiece 17 to a sealed mounting position as shown. When the needle is to be put to use, the safety jacket is rotated in order to disengage the guide tab 40 from the transverse extension 38 to a position where it is free to slide in the guide slot 36. The safety jacket 22 has a knurled or friction grip outer surface 19 for greater ease in handling. The safety jacket 22 is then moved endwise in the direction of the barrel 11, in this way forcing the needle to penetrate the end cap 33 to an exposed working position. In working position, if the needle is to be used for injection, the syringe body assembly can be manipulated by withdrawal of the plunger 12 so as to draw fluid through the needle into the chamber 13, unless the chamber has been previously filled. By use of the plunger manipulated by the operating disc 16 and handheld flange, fluid is ejected through the hypodermic needle for whatever use may be intended.

After use, the safety jacket 22 is then pulled longitudinally outwardly, withdrawing the needle 28 through the end cap 33 to the initial position entirely contained within the pocket 32. This position will be assured by engagement of the flange 42 with the shoulder 43, which at the same time will prevent separation of the safety jacket 22 from the needle-holding member 21. In this position the needle 23 is completely protected while the two parts of the needle attachment are being removed from the syringe body assembly and thereafter discarded. The syringe body assembly is then ready for reuse with another sanitized needle attachment.

In the embodiment of FIG. 6 the guide slot 36 and its transverse extension 38 are dispensed with and in their place there is provided a hole 50 through the wall of the safety jacket. On this occasion a guide tab 51 has a shoulder 52 which is adapted to abut against an adjacent side of the hole 50 in a semi-locked position. When the needle is to be projected through the end cap and the safety jacket shifted in position to accomplish this a camming surface 53, moving against an inside edge 54 of the hole 50, serves to resiliently expand the wall of the safety jacket 22 in a radial direction until the shoulder 52 clears the inside surface of the pocket 32. The needle, accordingly, can then be extended to its full working position.

After use, the safety jacket 22 is withdrawn outwardly until the guide tab 51 again enters the hole 50. The safety jacket is then anchored against further withdrawal while the needle attachment is withdrawn from the plunger in the manner heretofore made reference to.

In still another form of the invention, as shown in part in FIG. 7 the safety jacket 22' is provided with a modified wall 60 of resilient character from which an annular deflecting flange 61 extends into the pocket 32. In the initial assembled inoperative position of FIG. 7 the annular deflecting flange 61, extending inwardly from the modified wall 60 into the pocket 32, projects into an annular recess 62 in the head 63 of a needle-holding member 21'. Further, in the initial inoperative position, an annular shoulder 64 of the deflecting flange 61 engages against an annular shoulder 65 of the annular recess 62. In this position of the parts, the safety jacket 22' cannot be removed. When the needle 28 is to be exposed to a working position, the safety jacket is pushed toward the needle-holding member 21', causing the modified wall 60 to expand as the tapered side of the deflecting flange cams against the corresponding side of the annular recess, in this way enabling the needle to penetrate the end cap.

After the needle has served its purpose, the safety jacket 22' can then be pulled outwardly until the deflecting flange 61 again engages in the annular recess 62 where it is locked in position by engagement of the shoulders. A needle-holding member 21' of the type described in FIG. 7 can, if desired, be made an integral part of the barrel of the syringe body assembly. In an arrangement of the kind described in connection with FIG. 7, the expanded combination is one being capable of reuse or, on those occasions where reuse may be prohibitive, the entire assembly with the safety feature operative, may be discarded.

While particular embodiments of the present invention have been shown and described, it will be obvious to those skilled in the art that changes and modifications may be made without departing from the invention in its broader aspects and, therefore, the aims of its appended claims are to cover all such changes and modifications as fall within the true spirit and scope of this invention.

Having described the invention, what is claimed as new in support of Letters Patent is as follows:

1. A disposable needle attachment for use with a syringe body assembly which has an expulsion end and a handle end, said needle attachment comprising a needle-holding member having at one end a recess of constructing configuration for releasable sealing engagement with the syringe body assembly at said expulsion end and a needle-holding end for the mounting of a hypodermic needle, a reltively closed safety jacket member having a needle-receiving pocket, a permeable closure at one end of the jacket member for alignment with a free end of the needle, the other end of the jacket member having a variable connection to the needle-holding member, said jacket member having a protective first position relative to the needle-holding member adapted to entirely contain the needle and a second position wherein said needle is adapted to be exposed through said permeable closure in a work position, said jacket member being turnable to said protective first position wherein said disposable needle attachment is removable from said body assembly for disposal.

2. A disposable needle attachment as in claim 1 wherein there is a separate interlocking engagement between the jacket member and the needle-holding member operable when the jacket member is in said first position to prevent separation of said members during removal of said needle attachment from said syringe body assembly.

3. A disposbale needle attachment as in claim 1 wherein there is a plug removably disposed in said needle-holding member, said plug having attachment means for reception of a needle.

4. A needle attachment for use with a syringe body assembly which has an expulsion end and a handle end, said needle attachment comprising a needle-holding member and a relatively closed safety jacket member having a needle-receiving pocket, a permeable closure at one end of the jacket member for alignment with a free end of the needle, the other end of the jacket member having a variable connection to the needle-holding member, said jacket member having a protective first position relative to the needle-holding member adapted to entirely contain the needle and a second position wherein said needle is adapted to be exposed through said permeable closure in a work position, said jacket member being returnable to said protective first position, said variable connection comprising an aperture in the wall of the jacket member and a projection at the side of said needle holding member providing a shoulder for engagement with said aperture.

* * * * *